(12) United States Patent
Massey et al.

(10) Patent No.: US 7,306,574 B2
(45) Date of Patent: Dec. 11, 2007

(54) STEERABLE DILATATION SYSTEM, DILATOR, AND RELATED METHODS FOR STEPPED DILATATION

(75) Inventors: Joe B. Massey, Atlanta, GA (US); Phillip Jack Snoke, Winston Salem, NC (US)

(73) Assignee: Optivia Medical, LLC, Winston-Salem, NC (US)

( * ) Notice: Subject to any disclaimer, the term of this patent is extended or adjusted under 35 U.S.C. 154(b) by 389 days.

(21) Appl. No.: 10/268,500

(22) Filed: Oct. 10, 2002

(65) Prior Publication Data

US 2003/0135230 A1    Jul. 17, 2003

Related U.S. Application Data

(60) Provisional application No. 60/349,390, filed on Jan. 17, 2002.

(51) Int. Cl.
*A61M 37/00* (2006.01)
(52) U.S. Cl. .......................................... 604/95; 606/191
(58) Field of Classification Search ................ 606/190, 606/195; 604/95, 96, 164.09, 510; 600/139, 600/146, 182, 114
See application file for complete search history.

(56) References Cited

U.S. PATENT DOCUMENTS

| 4,954,129 A | 9/1990 | Giuliani et al. |
|---|---|---|
| D343,678 S | 1/1994 | Snoke et al. |
| D349,340 S | 8/1994 | Snoke et al. |
| 5,342,299 A | 8/1994 | Snoke et al. |
| 5,354,266 A | 10/1994 | Snoke |
| 5,399,164 A | 3/1995 | Snoke et al. |
| 5,423,311 A | 6/1995 | Snoke et al. |
| 5,437,636 A | 8/1995 | Snoke et al. |
| 5,496,269 A | 3/1996 | Snoke |
| 5,531,687 A | 7/1996 | Snoke et al. |
| 5,542,924 A | 8/1996 | Snoke et al. |
| 5,817,127 A | 10/1998 | Borodulin et al. |
| 5,860,953 A * | 1/1999 | Snoke et al. ............. 604/95.04 |
| 5,879,332 A * | 3/1999 | Schwemberger et al. ..................... 604/164.08 |
| 6,010,493 A * | 1/2000 | Snoke ........................ 604/510 |
| 6,213,974 B1 * | 4/2001 | Smith et al. ............. 604/95.01 |
| 6,234,958 B1 * | 5/2001 | Snoke et al. ................. 600/114 |
| 6,508,824 B1 * | 1/2003 | Flaherty et al. ............. 606/185 |
| 2001/0025134 A1 | 9/2001 | Bon et al. |
| 2002/0035373 A1 | 3/2002 | Carlson et al. |
| 2002/0040716 A1 | 4/2002 | Mandelkorn |

(Continued)

FOREIGN PATENT DOCUMENTS

| EP | 0 898 940 | 3/1999 |
|---|---|---|
| WO | WO 99 5353828 | 10/1999 |

*Primary Examiner*—Michael J. Hayes
*Assistant Examiner*—Nguyen Victor
(74) *Attorney, Agent, or Firm*—Bracewell & Giuliani LLP

(57) ABSTRACT

A dilatation system preferably including a dilator and a detachable handle for achieving step dilatation of a bodily opening is provided. The dilator preferably is steerable and can be visually guided using a fiber optic scope positioned in a lumen formed in a shaft of the dilator. Fluid can be delivered through the lumen with the scope positioned therein so as to distend, irrigate, or insufflate a space within the body. A kit and related methods also are provided that can include elements desired to facilitate step dilatation of a body opening.

13 Claims, 13 Drawing Sheets

U.S. PATENT DOCUMENTS

2002/0087152 A1 7/2002 Mikus et al.
2002/0099258 A1 7/2002 Staskin et al.
2002/0133128 A1 9/2002 Heller
2002/0137988 A1 9/2002 Shipp et al.

* cited by examiner

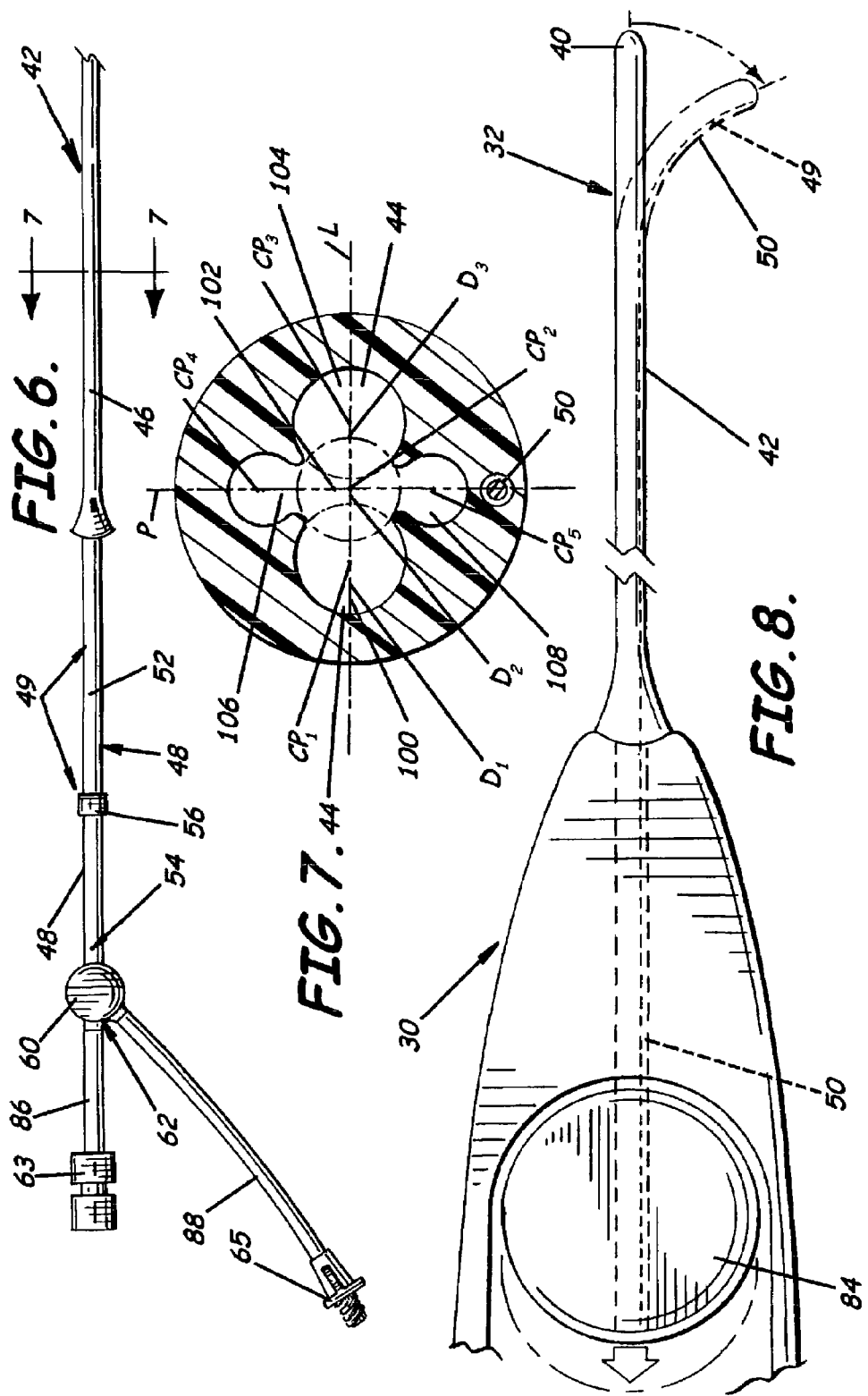

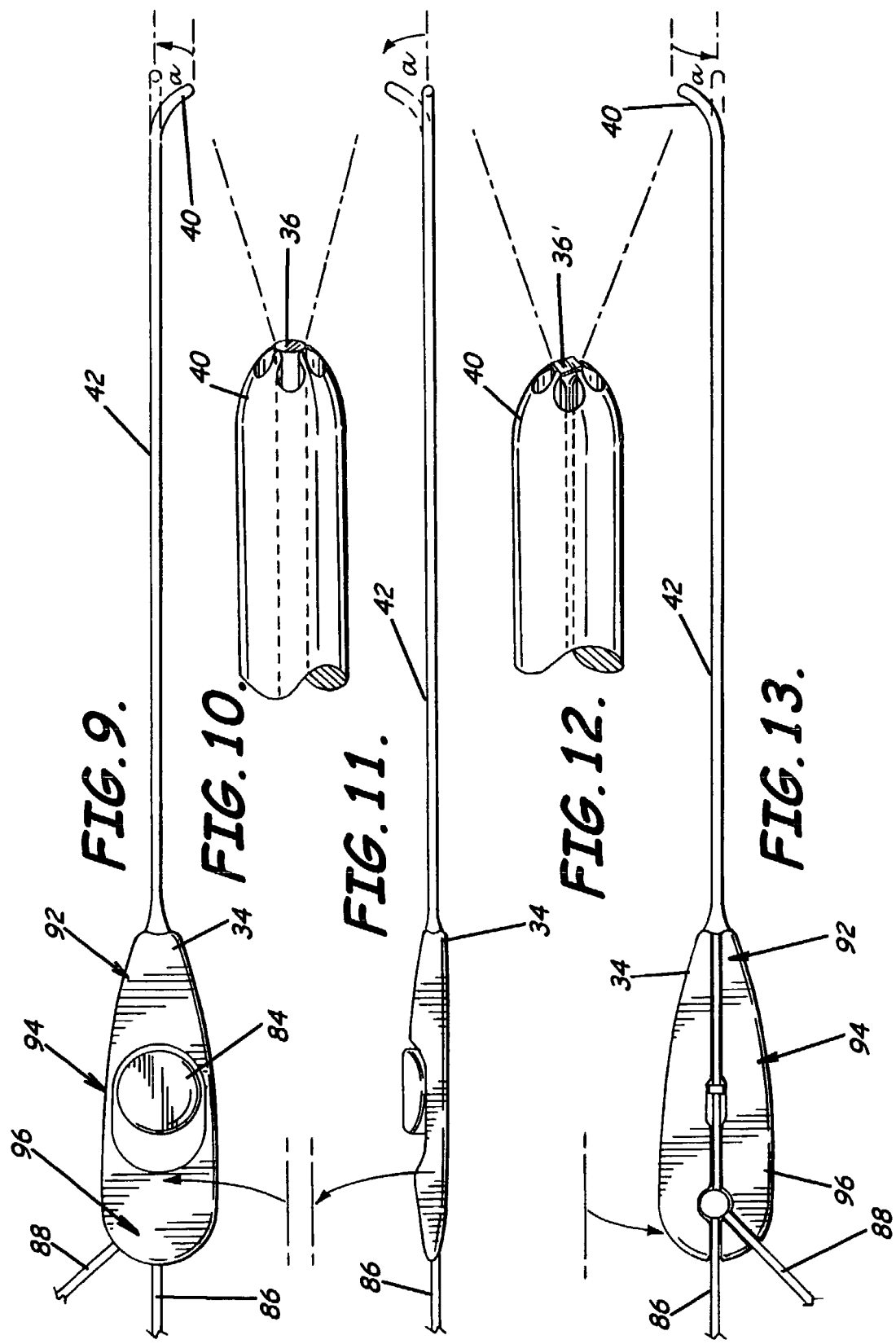

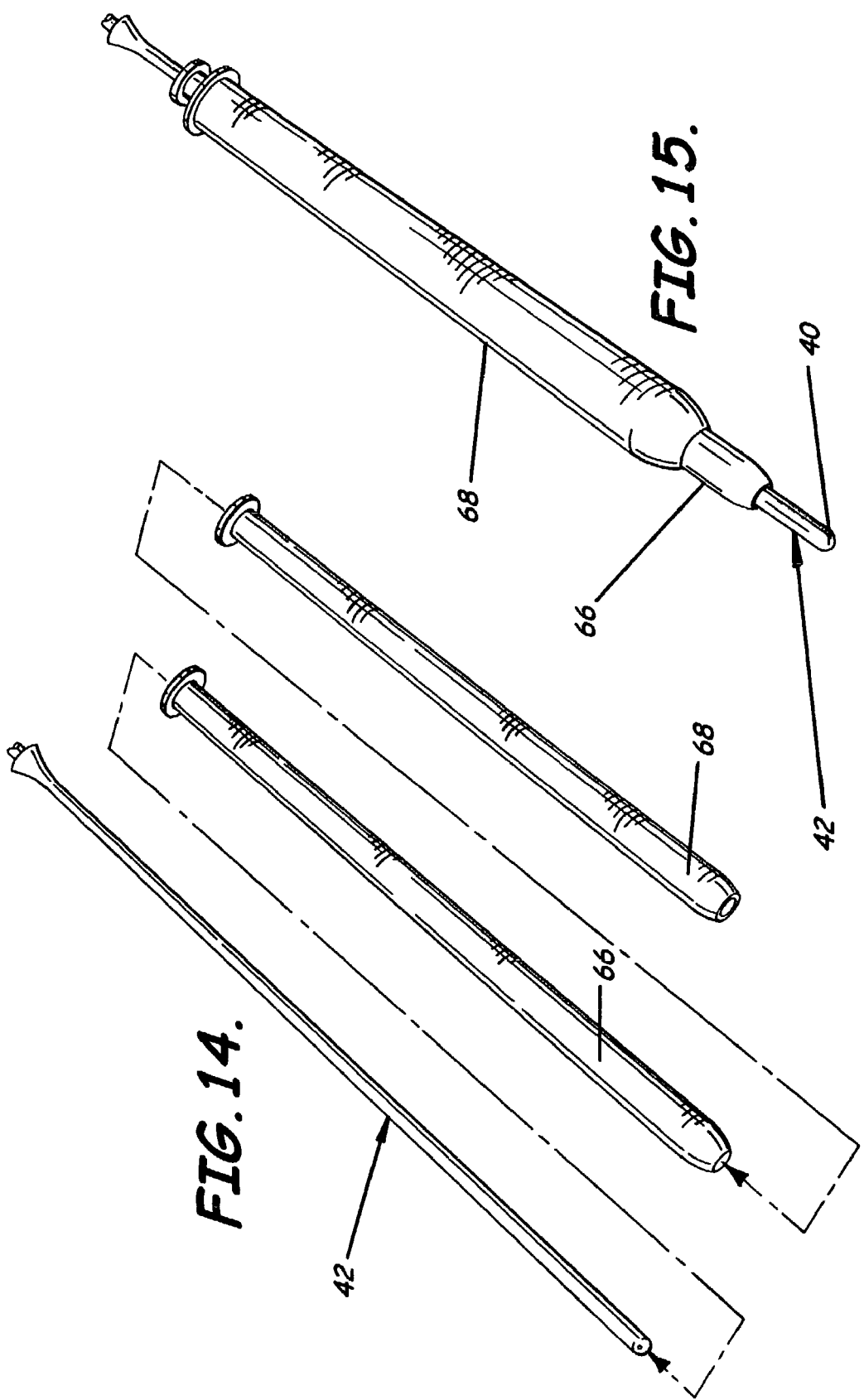

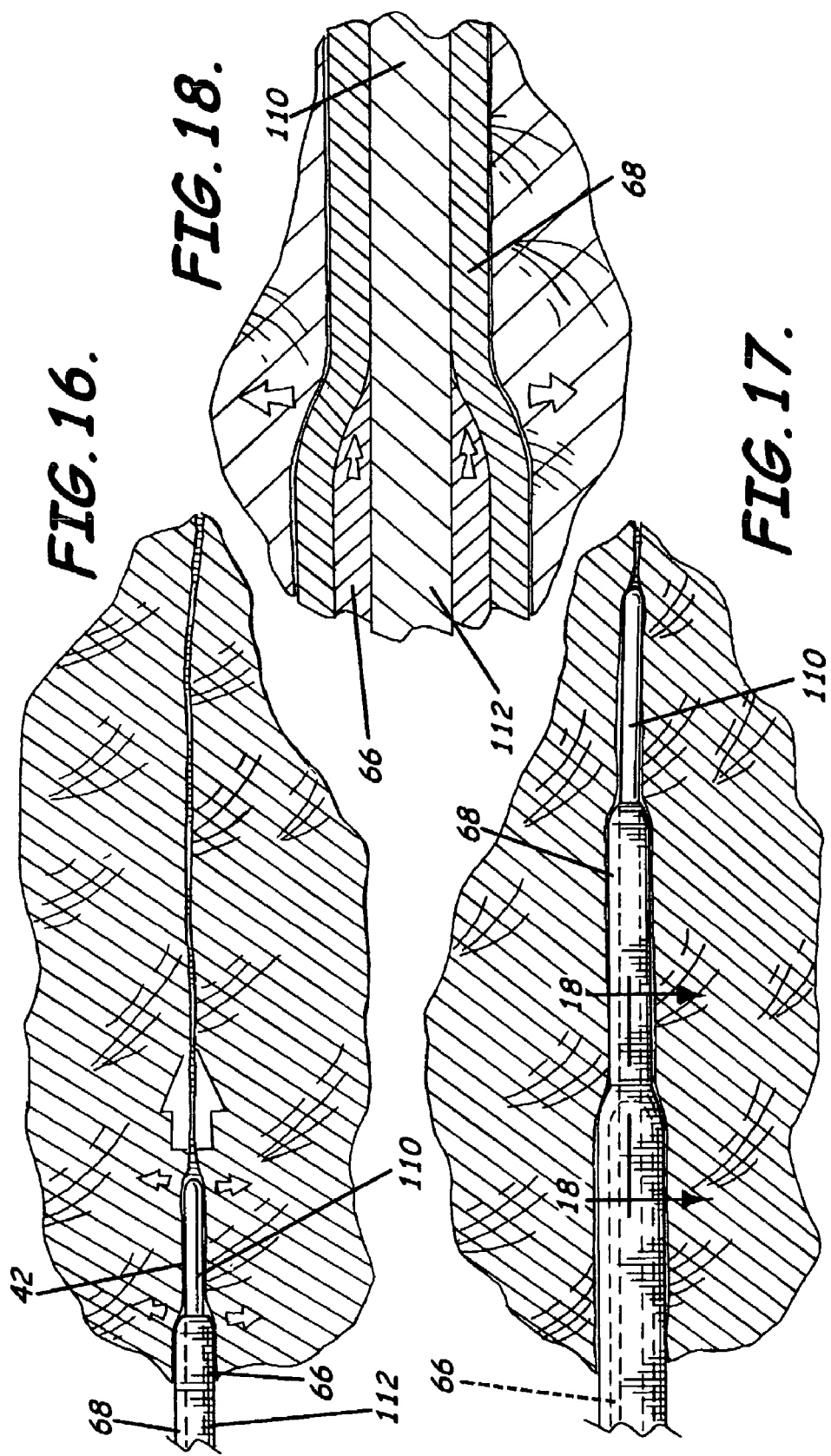

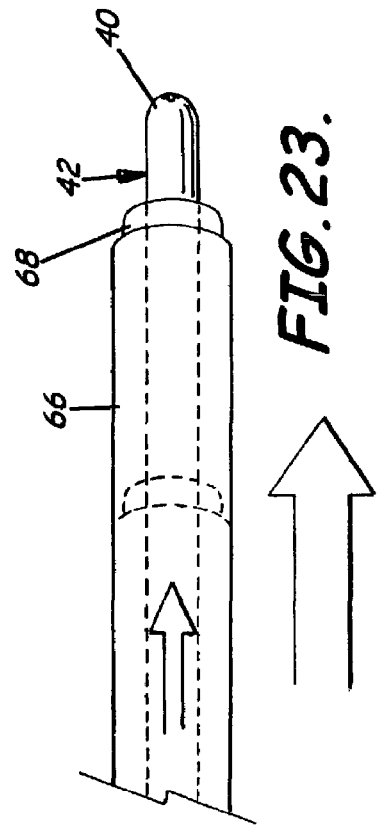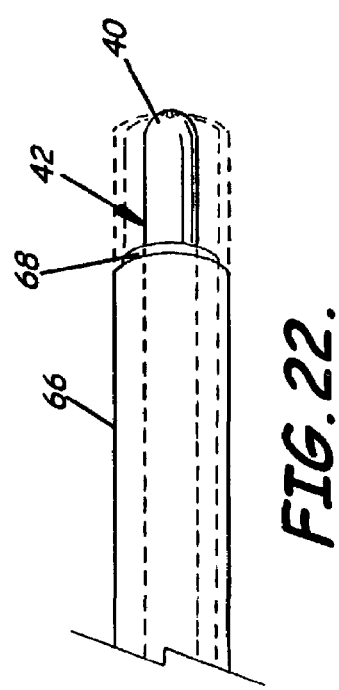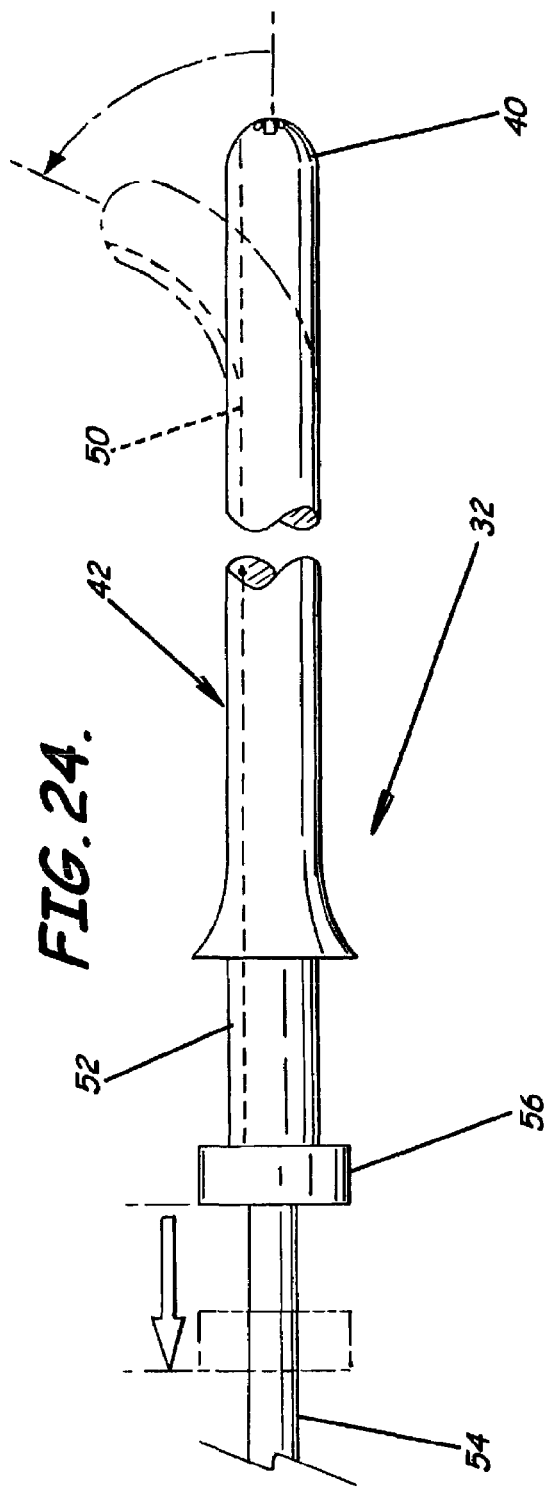
FIG. 23.
FIG. 22.
FIG. 24.

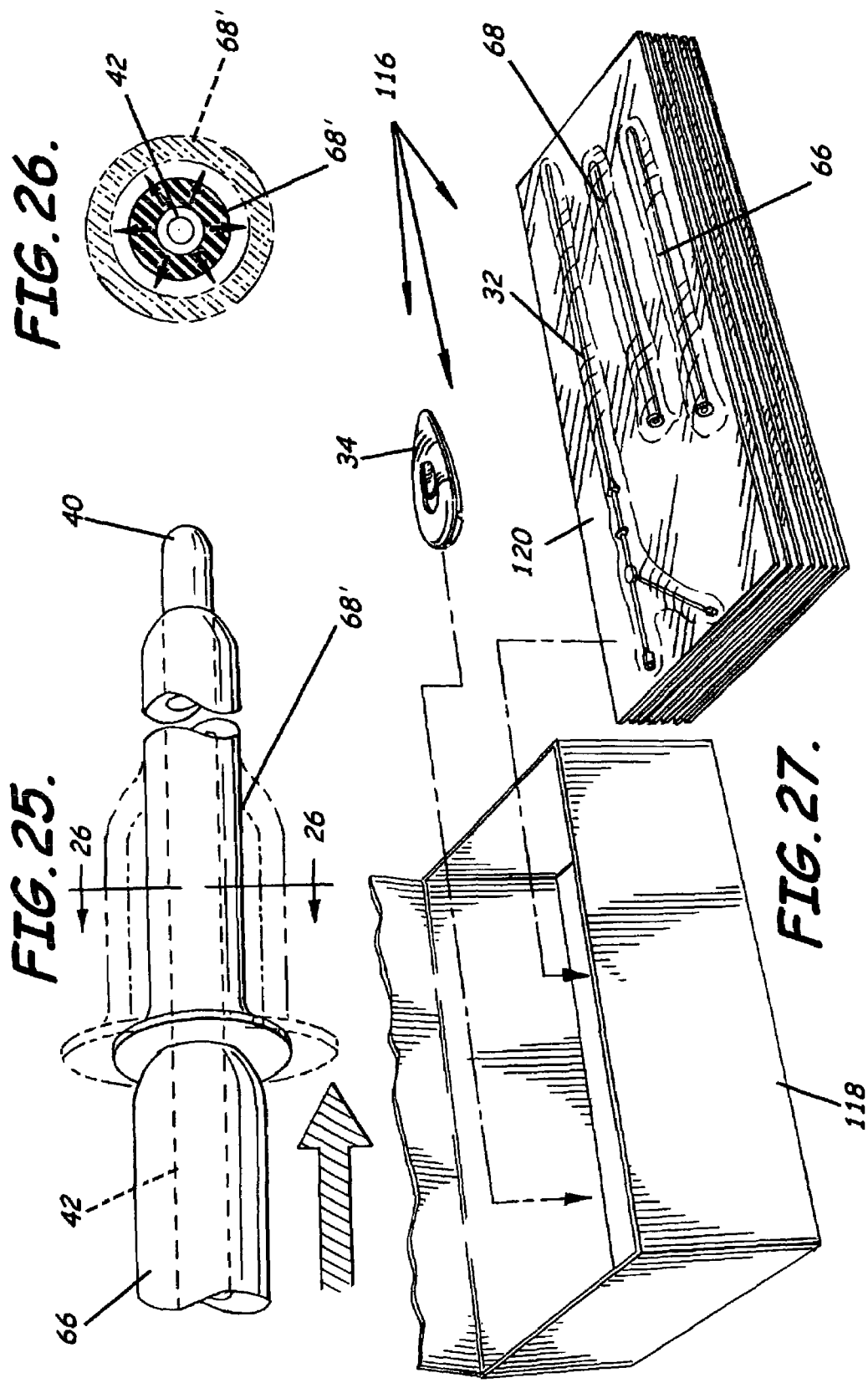

STEERABLE DILATATION SYSTEM, DILATOR, AND RELATED METHODS FOR STEPPED DILATATION

RELATED APPLICATIONS

This is a non-provisional patent application which claims the priority of provisional patent application U.S. Ser. No. 60/349,390, filed Jan. 17, 2002, and titled Steerable Dilatation System, Dilator, and Related Methods for Stepped Dilatation, which is incorporated herein by reference in its entirety.

FIELD OF THE INVENTION

The present invention relates generally to medical dilators and, more specifically, to a steerable dilator for dilating a cavity, canal, blood vessel, or other opening in a human or animal body.

BACKGROUND OF THE INVENTION

Physicians and veterinarians frequently rely on methods of dilatation of a natural opening in a body (e.g., the urethra) to gain greater access to internal areas of the body without making an incision and cut through tissue of the body. A not infrequent purpose of this procedure of dilating a cavity, canal, duct, blood vessel or other bodily opening is to enlarge the opening so as to permit the insertion of instruments through the opening for visualization, tissue sampling, or therapeutic treatment of areas of the body accessible through the opening.

Conventional devices for effecting dilatation in a body include sized metal rods with fixed angles. Other such devices are metallic instruments that can be bent to conform to a selected portion of the body. Still other conventional dilators are made of malleable polymeric material.

A serious drawback of these conventional devices recognized by Applicants is that they necessitate the physician's estimating how far into the body the device extends and where within the body the device is positioned. This limitation forces a physician using such a device to slowly probe with the tip of the device inside a patient's body as the device is inserted into the body. Accordingly, the physician must rely largely on tactile sensations to judge whether the instrument is being properly maneuvered within the patient's body. This poses the ever-present risk that if the physician misjudges the position of the dilatation device, the wall of cavity or organ may be perforated.

Another drawback of these conventional devices recognized by Applicants is that they pose a difficult economic choice in the sense that each dilatation device must be either disposed of after only one use—in which case, each such device will need to be relatively inexpensive to manufacture—or otherwise it must be sterilized. Sterilization is a consideration that must be addressed with any reusable medical device, but is especially pertinent with respect to those used in invasive procedures. Viruses and bacteria can be trapped on the surfaces of such devices. Moreover, the lubricants applied during the use of such devices, if they remain on the device's surface, can trap microbes on the surface. If the devices are to be reused safely, some means of sterilizing the devices are an absolute essential. Sterilization methods are available for reusable medical devices. Heat or chemicals such as glutaraldehyde can be used. These methods, however, can be expensive and can reduce the operative life of the instrument. Moreover, there is a growing recognition by others that repeated use of antibiotics for sterilization (and other) purposes can reduce their effectiveness. The only alternative to sterilization, therefore, is to make the device completely disposable. Applicants have also recognized, however, that disposable can be out of the question from a purely economic standpoint if the device is to include the advanced features needed to overcome the limitations of conventional dilatation devices.

Accordingly, there is a need for a dilator that can be accurately guided through tortuous actual and potential spaces, canals, and cavities of the body without relying on elaborate structures and mechanisms that would make disposal or sterilization of the device cost prohibitive.

SUMMARY OF THE INVENTION

With the foregoing in mind, the present invention provides a dilatation system, dilator apparatus, and related dilatation methods that provide for visually guided, fluid facilitated dilatation of a bodily opening. The present invention, moreover, provides advantageous features with a structure that not only provides advanced capabilities over conventional dilators but is also economical to make. Specifically, the dilator is made so that it can be detachably connected to either a reusable or disposable handle. Because the dilator, though having advanced capabilities, is economical to make, it can be used once and disposed of so as to avoid the expense of sanitization. The handle is designed so as to facilitate easy and economical sanitization if desired; it thus can be economically re-used. Thus, the present invention provides a system including an economically made dilator having visualization and fluid distension capabilities coupled with a detachable re-usable handle so as to facilitate dilatation that is simultaneously more advanced than conventional devices and more economical to produce.

The dilatation system according to the present invention preferably includes a dilator, a detachable handle, a fiber optic scope and a fluid delivery supply. The dilator preferably includes a dilatation shaft having a malleable distal portion that includes a flexible distal tip. The dilatation shaft preferably also includes a proximal portion and, associated therewith, a controller to control the attitude of the flexible distal tip of the dilatation shaft.

The controller, for example, can be provided by a control sleeve connected to at least one control wire extending axially from the distal tip to the proximal portion of the dilatation shaft on which the control sleeve can be slidably positioned. The proximal portion of the dilatation shaft can include a distal region having a distal region diameter and a proximal region having a proximal region diameter. The distal region diameter preferably is greater than the proximal region diameter. The control sleeve preferably substantially surrounds the proximal region so as to slidably move over the proximal region to thereby increase tension in the at least one control wire and cause the distal tip of the dilatation shaft to flex in response thereto. As more fully understood in the context of other features of the dilator and the detachable handle yet to be discussed, this structure provides control necessary to steer the dilatation shaft within the contours and potential spaces of a bodily opening and yet is easily attached to a detachable handle. Within the dilatation shaft, a lumen preferably extends axially through the shaft.

Preferably, a perimeter of a sectional boundary of the dilatation shaft, the section being taken substantially perpendicular to a longitudinal axis extending through the center of the lumen, defines a cavity having a central portion around which are positioned a plurality of spaced-apart lobes. The lumen, for example, can be formed by an intersection of five substantially cylindrical-shaped openings so that the perimeter of the lumen defines a cavity having a central portion around which are positioned four spaced-apart lobes. The perimeter of the lumen permits a flexible fiber optic scope to be positioned in the dilatation shaft so that it extends axially substantially through the central portion of the lumen while also permitting fluid to be delivered through the lumen. Thus, the dilator can be visually guided as it is advanced within a bodily opening, visualization being provided by the fiber optic scope position in the lumen of the dilatation shaft. Tissue and collapsed potential space within the body, moreover, can be irrigated, insufflated, and distended by the fluid delivered through the lumen within which the fiber optic scope is positioned. To reduce resistance to the advancement of the dilator within a body opening and also further facilitate the delivery of fluid through the lumen with the fiber optic scope positioned therein, the tip of the dilatation shaft is preferably tapered. With respect to this latter feature, specifically, tapering exposes the perimeter of each lobe of the lumen so that the opening has a substantially elliptical shape thereby facilitating delivery of fluid through the lumen.

The dilator, for example, also can include a manifold attached to a proximal end of the dilatation shaft. The manifold, moreover, can include at least one access port in fluid communication with the lumen of the dilatation shaft. Preferably, the at least one access port includes at least a first and a second access port attached to which, respectively, is a first supply tube and a second supply tube. The fiber optic scope can be extended through the first supply tube into the lumen and extended through the lumen to the distal tip of the dilatation shaft. A fluid delivery supply can deliver fluid to the lumen through the second supply tube.

As already noted, a distinct advantage of the present invention is that the dilator, though providing visualization and fluid distension, insufflation, and irrigation capabilities can be made economically so that it need not be sterilized but rather is simply disposed of after a single use. The dilator, however, is adapted to detachably connect to a reusable or disposable handle. The handle according to the present invention easily connects to the dilator and, more specifically, engages the controller associated with the dilatation shaft and distal tip. Preferably, the handle includes a dilatation channel formed in the handle so that the dilatation shaft can be readily received and retained therein. The handle preferably also includes a manifold channel formed in the handle to receive and retain therein the manifold of the dilator. The handle further preferably includes at least one supply tube channel also formed in the handle to receive and retain therein the at least one supply tube connected to the manifold of the dilator.

A particular advantage provided by the handle is a control actuator positioned thereon and adapted to readily engage the controller associated with the dilator when the dilator is detachably connected with the handle. Specifically, the control actuator preferably is positioned to be responsive to finger or thumb deflection supplied by a user holding the handle and controllably steering the dilator using a single hand.

The system and, in particular, the dilator of the present invention advantageously enable distinct methods of dilating a bodily opening in a step-dilatation manner. According to one such method, a distal region of a dilatation shaft is inserted into an opening in the body while on a proximal region of the shaft is slidably positioned at least one spacer and a cannula. The at least one spacer then is slidably moved over at least a portion of the distal region of the shaft while the cannula remains positioned at the proximal region of the shaft. The radial diameter of the at least one spacer is greater than that of the dilatation shaft so that advancing the spacer into the opening over the distal region of the shaft dilates the opening. The cannula is then slidably moved over at least a portion of the spacer while the spacer remains in position over the distal region of the shaft.

Alternatively, step dilatation can be achieved using a cannula having at least a medial portion adapted to radially expand. According to this method, the cannula is slidably positioned on the shaft of the dilator and the dilator and cannula inserted into a body opening. A spacer is selected to have a larger radial diameter than that of the cannula and the dilator shaft is withdrawn leaving the cannula within the body opening. The spacer is slidably positioned over the shaft and inserted into the cannula positioned within the bodily opening to thereby radially expand the cannula.

Step dilatation according to either method can be enhanced by visualizing an actual or potential space within the body using a fiber optic scope (or camera-tipped scope or other imaging-tipped scope) positioned within the lumen formed in the dilatation shaft. Each method further can be enhanced by irrigating and/or distending tissue within the body with a fluid, e.g., gas or liquid, delivered via the lumen of the shaft. Specifically, the fluid delivered into the body aids step dilatation in a number of distinct ways. The fluid, for example, can provide increased lubricity in and around the dilator, easing the advancement of the dilatation shaft. The fluid, moreover, also creates fluid pressure against the cavity walls and tissue. Thus, as the dilator is advanced into the body and as step dilatation proceeds within a bodily opening the pressure of the fluid introduced into the body increases, thereby adding to the forces tending to distend tissue and further dilate the bodily opening. Accordingly, the fluid delivery can irrigate a passage for the dilator and also can provide fluid pressure that cooperates with the forces provided by the spacer and the cannula in dilating the bodily opening.

The present invention also provides a disposable dilator kit usable by a physician, veterinarian, or other qualified medical personnel to dilate a portion of a human or an animal body opening with a visually guided, fluid facilitated steerable dilator. The kit provides a distinct benefit, for example, in that it provides a single convenient source of elements necessary for inducing dilatation in a patient. The kit can conveniently be positioned within ready reach of an attending physician or other qualified medical personnel. Moreover, the kit can be conveniently transported by a physician, physician's assistant, or nurse to a site where dilatation is to be induced in a patient.

The kit preferably includes a disposable container having a sanitized disposable steerable dilator in a sanitary dilator package positioned therein. The kit container preferably also includes a sanitized handle adapted to detachably connect to the dilator and contained in a sanitary handle package. Moreover, the kit container preferably also includes a sanitized cannula contained in a sanitary package and adapted to be slidably positioned over at least a portion of the dilatation shaft of the dilator. The kit container, moreover, preferably includes also at least one spacer contained in a sanitary package and adapted to be slidably positioned over at least a portion of the dilator and to be positioned within the cannula.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 6 is a fragmentary perspective view of a dilator having dilatation shaft, control sleeve, manifold, and supply tubes according to the present invention;

FIG. 7 is sectional view taken along line 7-7 of FIG. 6 of a dilatation shaft and lumen according to the present invention;

FIG. 8 is a fragmentary top plan view of a dilator and detachable handle for accomplishing guided stepped dilatation according to the present invention;

FIG. 9 is a fragmentary top plan view of a dilator and detachable handle for accomplishing guided stepped dilatation according to the present invention;

FIG. 10 is a fragmentary perspective view of a distal tip of a dilatation shaft and a fiber optic scope positioned within a lumen of the dilatation shaft according to the present invention;

FIG. 11 is a fragmentary side elevation view of a dilator and detachable handle for accomplishing guided stepped dilatation according to the present invention;

FIG. 12 is a fragmentary perspective view of a distal tip of a dilatation shaft and a camera chip on a tip of an imaging device positioned within a lumen of a dilatation shaft according to a second embodiment of the present invention;

FIG. 13 is a fragmentary bottom plan view of a dilator and detachable handle for accomplishing guided stepped dilatation according to the present invention;

FIG. 14 is a fragmentary exploded perspective view of a distal portion of a dilatation shaft, spacer, and cannula of dilator for accomplishing stepped dilatation according to the present invention;

FIG. 15 is a fragmentary perspective view of a distal portion of a dilatation shaft having a spacer positioned thereon and a cannula positioned on the spacer and distal portion of the dilatation shaft for accomplishing stepped dilatation according to the present invention;

FIG. 16 is a fragmentary environmental side elevational view of a dilator according to the present invention;

FIG. 17 is a fragmentary environmental side elevational view of a dilator according to the present invention;

FIG. 18 is an enlarged sectional view taken along line 18-18 of FIG. 17 of a dilator according to the present invention;

FIG. 22 is a fragmentary side elevational view of a dilator including a dilatation shaft along with a spacer and a cannula slidably positioned thereon according to the present invention;

FIG. 23 is a fragmentary side elevational view of a dilator including a dilatation shaft along with spacer and cannula slidably positioned thereon according to the present invention;

FIG. 24 is a fragmentary side elevational view of a dilatation shaft having a slidable control sleeve, a proximal portion having a distal region with a distal region diameter, and a proximal portion having a proximal region with a proximal region diameter according to the present invention;

FIG. 25 is a fragmentary side elevational view of another embodiment of a dilator including dilatation shaft, spacer, and cannula having a radially expandable portion according to the present invention;

FIG. 26 is a sectional view taken along line 26-26 of FIG. 25 of another embodiment of a dilator including dilatation shaft, spacer, and cannula having a radially expandable portion according to the present invention;

FIG. 27 is an environmental perspective view of a sanitized dilatation kit according to the present invention;

DETAILED DESCRIPTION

Figure 1:
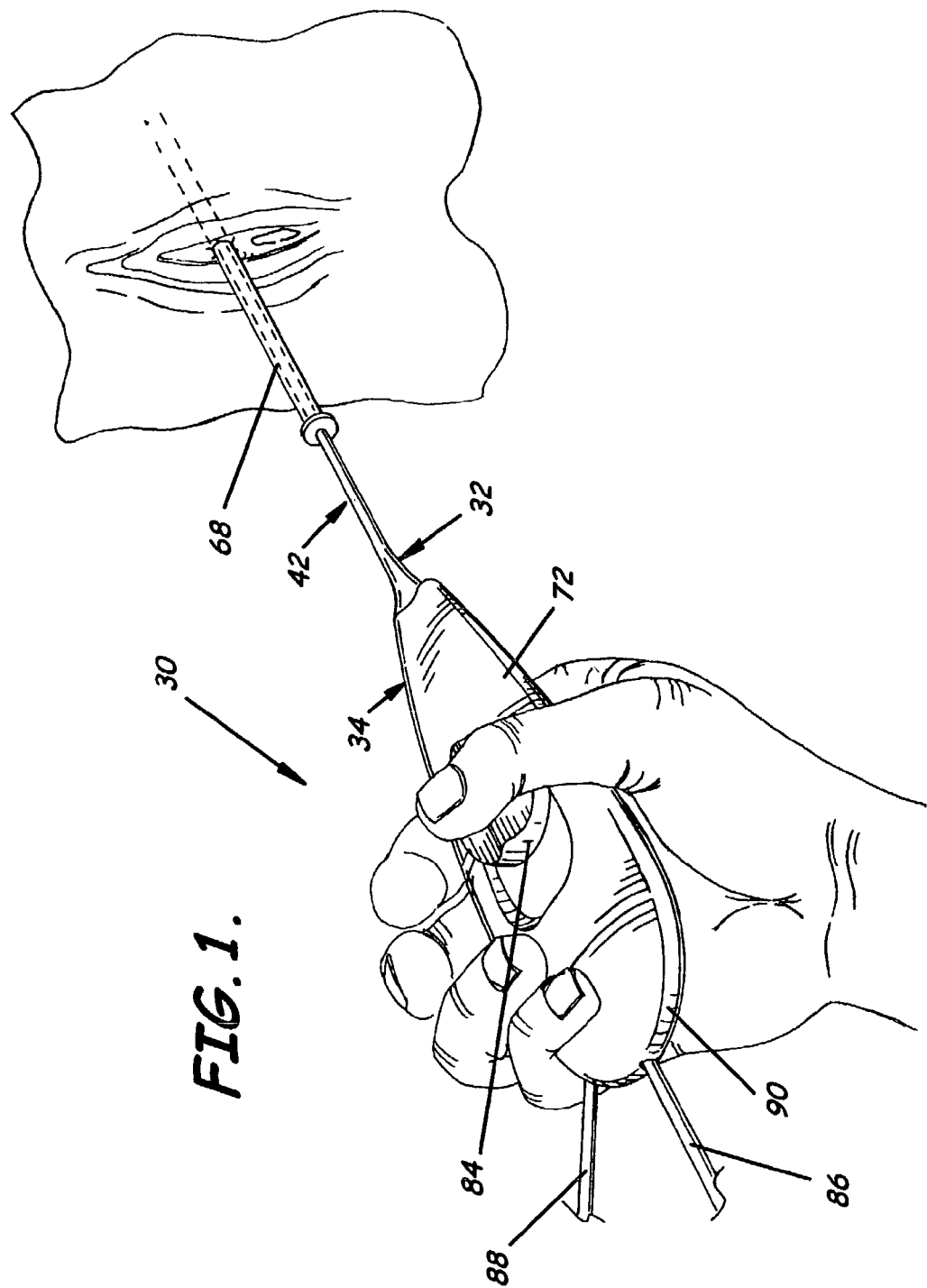
FIG. 1 is a perspective environmental view of a steerable dilator and detachable handle for accomplishing guided stepped dilatation according to the present invention.
Figure 2:
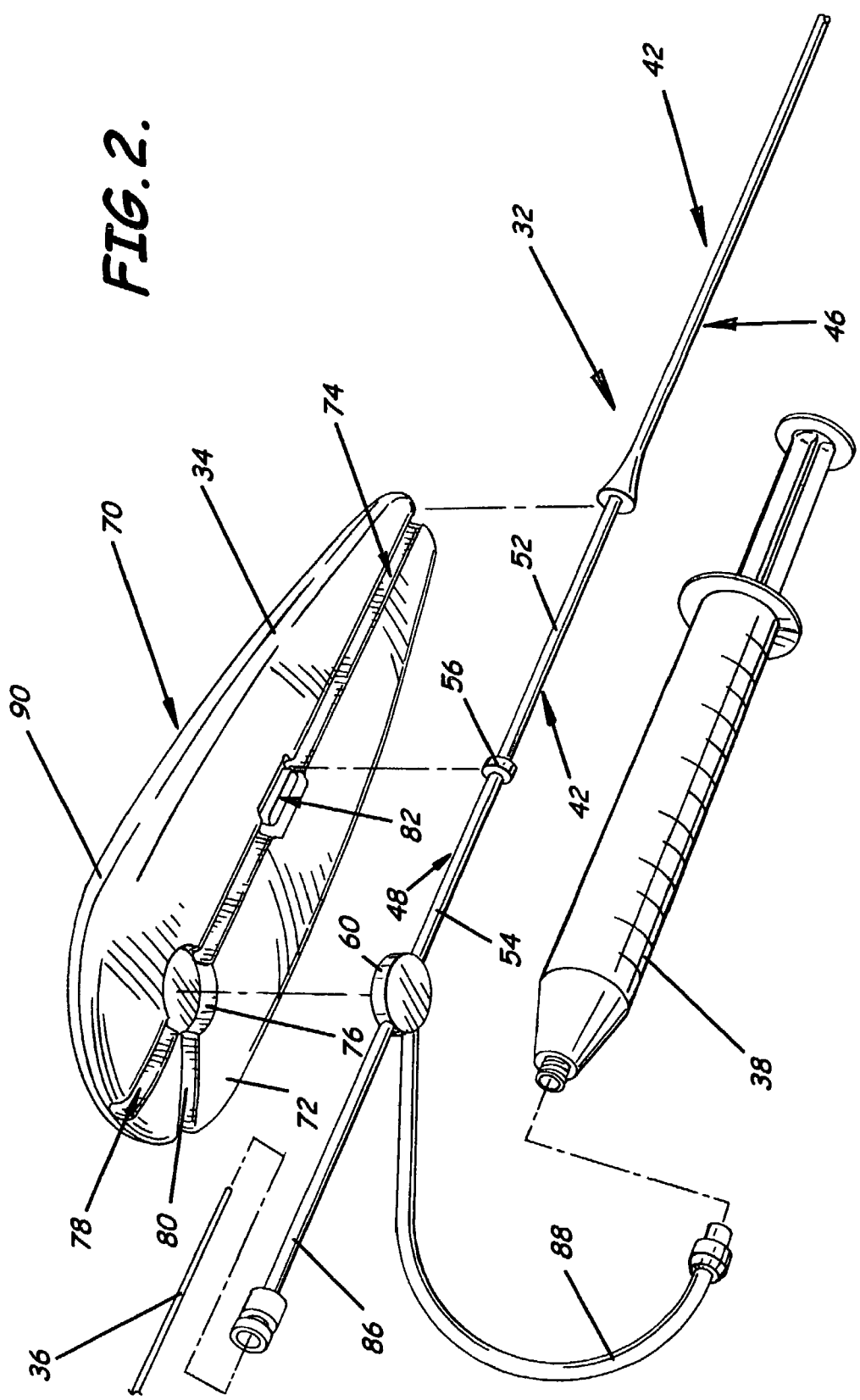
FIG. 2 is an exploded perspective view of a steerable dilatation system for accomplishing guided stepped dilatation according to the present invention.
Figure 3:
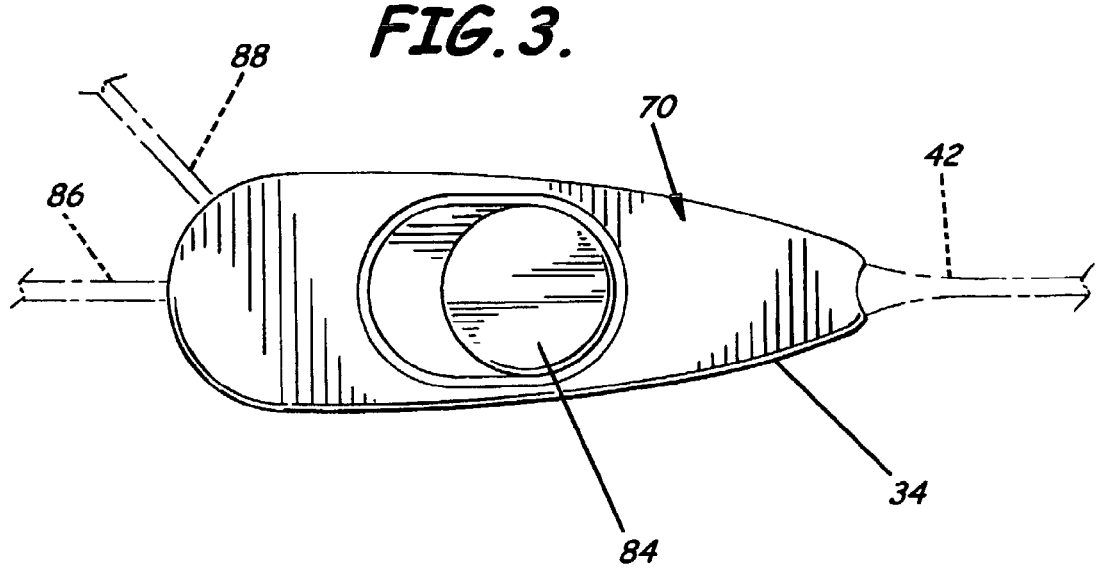
FIG. 3 is a top plan view of a handle of a steerable dilator for accomplishing guided stepped dilatation according to the present invention.
Figure 4:
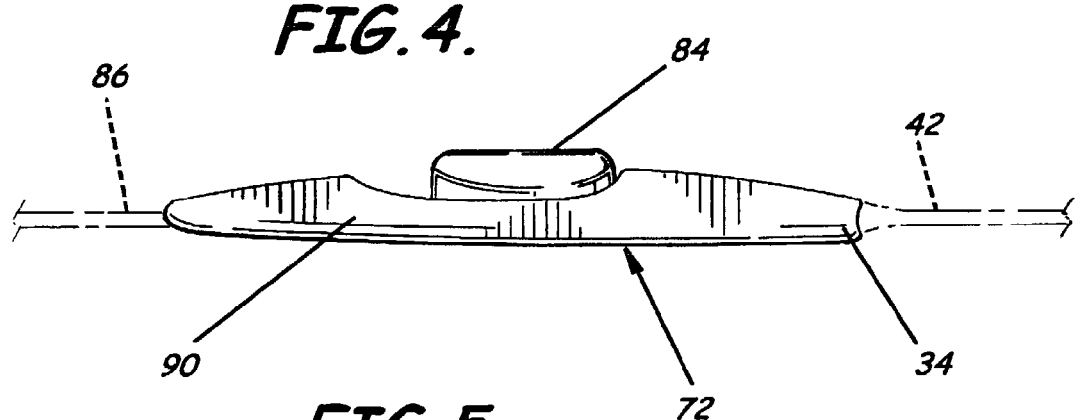
FIG. 4 is a side elevation view of a handle of a steerable dilator for accomplishing guided stepped dilatation according to the present invention.
Figure 5:
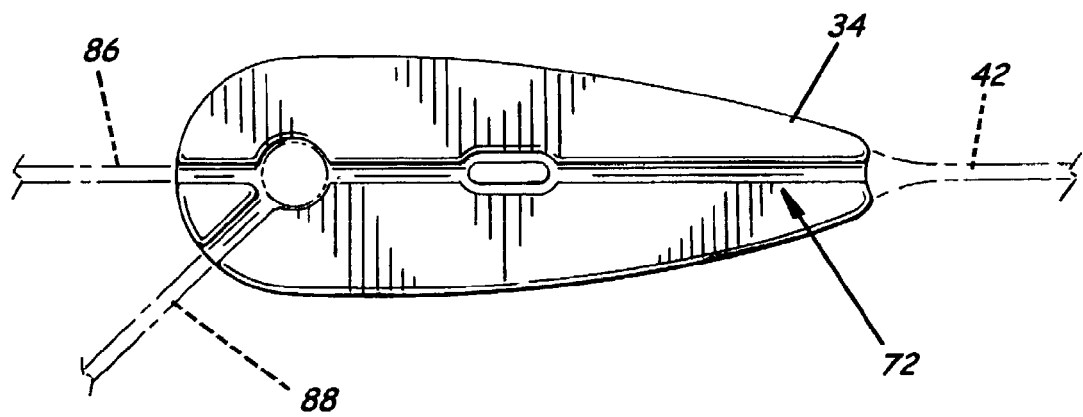
FIG. 5 is a bottom plan view of a handle of a steerable dilator for accomplishing guided stepped dilatation according to the present invention.

The present invention will now be described more fully hereinafter with reference to the accompanying drawings which illustrate preferred embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. The prime notation, if used, indicates similar elements in alternative embodiments.

FIGS. 1, 2, and 6-13 illustrate a visually guided steerable stepwise dilatation system 30 for use in dilating a cavity, canal, blood vessel, or actual or potential space within a human or animal body. The system preferably has a dilator 32, a handle 34, a fiber optic scope 36, camera on a scope 36', or other imaging device, and a fluid supply 38. The dilator 32, specifically, is a steerable dilator that, as explained herein, preferably has a dilatation shaft 42 including a flexible tip 40 and malleable distal portion 46 to permit the dilator 32 to be steered within a potential space of the body and to conform to internal bodily contours. The dilator 32 preferably includes a lumen 44 through which the fiber optic scope 36 (or camera on a scope 36') can be extended to visualize position and movement of the dilator 32 within the body. Fluid supplied by a fluid supply 38, e.g., a syringe, a bag, a reservoir, or other fluid source, also can be delivered through the lumen 44 to distend and/or irrigate and/or insufflate an actual or potential space in the body.

The steerable dilator 32 preferably has the dilatation shaft 42. The shaft preferably is a substantially elongate steerable shaft having, in addition to the malleable distal portion 46 and flexible distal tip 40, a medial portion 48 that preferably is at least slightly more rigid than the malleable distal portion 46. To control the attitude of the flexible distal tip 40, the dilator 32 preferably includes a controller 49. Preferably, the controller 49 includes at least one control wire 50 (see FIGS. 7-8 preferably connected to the distal tip 40 of the dilatation shaft 42 and extending axially from the distal tip 40 parallel with the longitudinal axis of the dilatation shaft 42 toward the proximal end of the dilatation shaft 42. The controller 49, preferably, is connected to a proximal end of the dilatation shaft 42 at least one control wire 50 by one of various attachment techniques as understood by those skilled in the art.

The controller 49 is preferably positioned on or adjacent the medial portion 48 of the dilatation shaft 42. Preferably, the controller 49 is a ball joint, flange, tab, or other control-wire-connected device movingly connected to the medial portion 48 of the dilatation shaft 42 so as to control the movement of the distal tip 40 to be manually actuated by a user of the dilator 32. For example, the controller 49 can slidingly move parallel to the longitudinal axis of the dilatation shaft 42 and thereby increases the tension on the control wire 50 so as to flex the flexible distal tip 40. Also, for example, the controller 49 can be provided by a control sleeve 56 (or control-wire-connected collar) that slidably extends around the medial portion 48 of the dilatation shaft 42. When the control sleeve 56 is slidably moved over the dilatation shaft 42 in a direction parallel to the longitudinal axis of the shaft, the resulting tension in the control wire 50 causes the flexible distal tip 40 to flex in response thereto. Thus, the control sleeve 56 controls the attitude of the distal tip 40 of the dilatation shaft 42 of the dilator 32 (see FIGS. 8-9, 11, and 13).

Preferably, the medial portion 48 of the dilatation shaft 42 is formed so that a distal region 52 of the medial portion 48 has a distal radial diameter and a proximal region 54 of the medial portion 48 has a proximal radial diameter. More preferably, the distal radial diameter of the distal region 52 is greater than the proximal diameter of the proximal region 54 of the medial portion 48 of the dilatation shaft 42. Accordingly, the at least one control wire 50 connected at its distal end to the distal tip 40 of the dilatation shaft 42 and extending axially parallel to the longitudinal axis of the dilatation shaft 42 preferably is positioned within at least the distal portion 46 of the dilatation shaft 42. The at least one control wire 50 then preferably also extends within the distal region 52 of the medial portion 48 of the dilatation shaft 42 as well. The at least one control wire 50 thus can extend outwardly from the distal region 52 of the medial portion 48 of the dilatation shaft 42 to connect to the control sleeve 56 and be slidably positioned to substantially surround the proximal region 54 of the medial portion 48.

The control sleeve 56 connected to a proximal end of the control wire 50 as understood by those skilled in the art and slidably positioned to substantially surround a portion of the proximal region of the medial portion of the dilatation shaft 42 is thus positioned to control the attitude of the distal end of the dilatation shaft 42 when slidably moved axially along the proximal region 54 of the medial portion 48 of the dilatation shaft 42.

Figure 28:
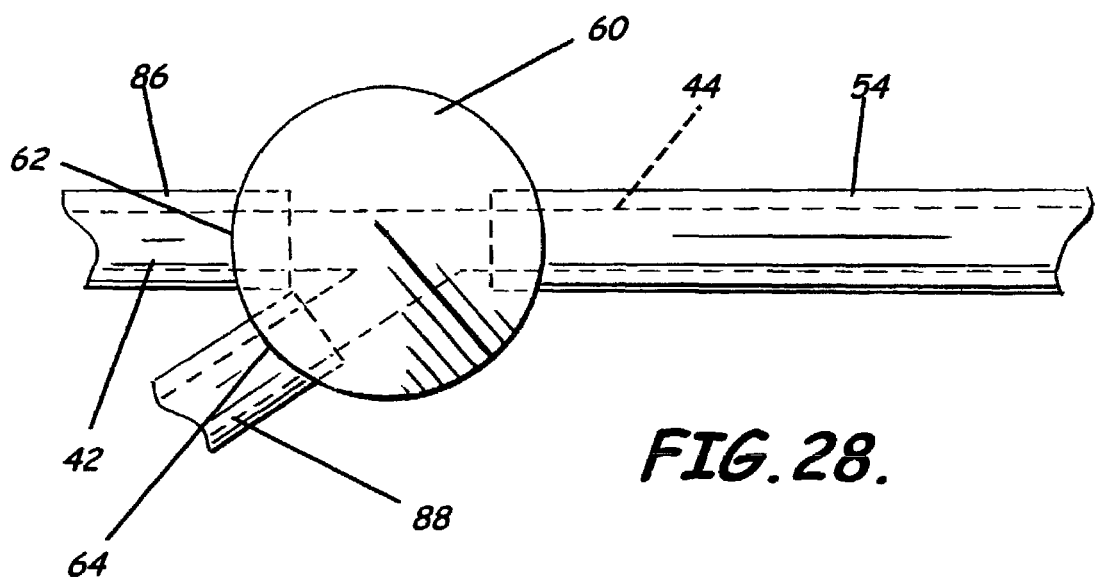
FIG. 28 is an enlarged fragmentary view of a manifold of a dilator according to the present invention.
Figure 29:
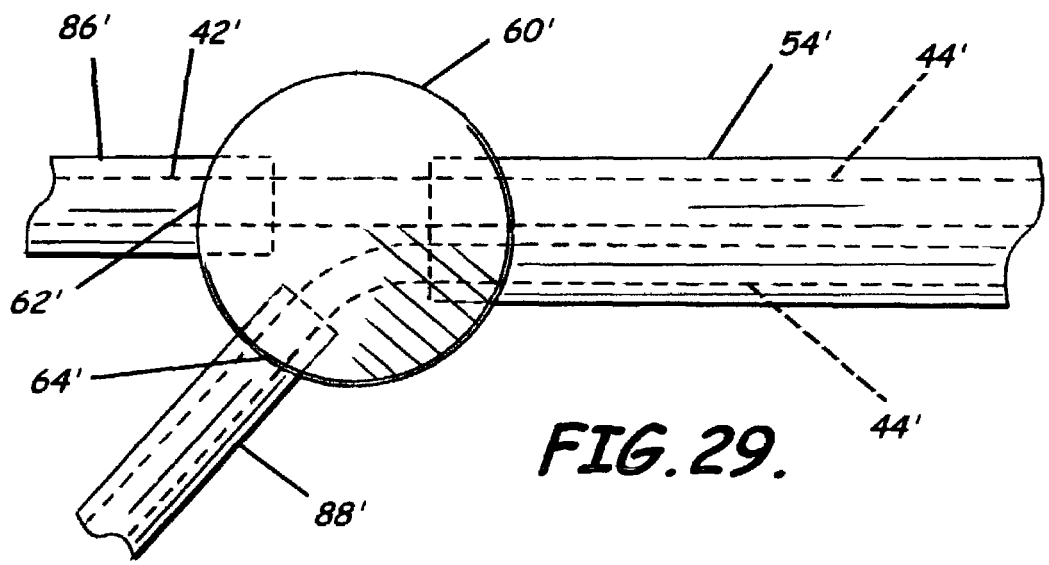
FIG. 29 is an enlarged fragmentary view of another embodiment of a manifold of a dilator according to the present invention.

The dilator 32 preferably also includes a manifold 60, 60' connected to a proximal end of the proximal region 54 of the medial portion 48 of the dilatation shaft 42 (see FIGS. 28-29). The manifold 60, 60' preferably has at least a first and a second access port 62, 64 formed therein. The manifold 60, 60' is preferably made to be both air-tight and water-tight for reasons explained more fully below.

The lumen of the dilator 32 is at least one dilatation shaft lumen 44, 44', e.g., preferably one 44 but two 44' or more can be used as well, extending from the manifold 60 axially through the dilatation shaft 42 to the distal tip 40 of the dilatation shaft 42. Preferably, such as shown in FIGS. 6-7, the lumen 44 is formed so that a sectional boundary of the lumen 44, formed by taking a cross-section substantially perpendicular to a longitudinal axis extending through the center of the lumen 44, defines the perimeter of a cavity having a central or medial portion 102 substantially surrounding or adjacent which are positioned a plurality of spaced-apart lobes 100, 104, 106, 108. So structured, the lumen 44 provides a center region through which a fiber optic scope 36, camera-tipped scope 36', or other imaging device can extend (see FIGS. 10 and 12). At the same time, the enlarged peripheral regions formed by the lobes 100, 104, 106, 108 (see FIG. 7) permit fluid to be supplied through the lumen 44 even when a scope 36 is positioned therein. The fiber optic scope 36 (or camera-tipped scope 36' or other image-tipped or image-gathering scope) preferably positioned within the lumen 44, as explained more fully below, provides visualization of the bodily region in which the dilatation shaft 42 is positioned and maneuvered, thus obviating the need for the user of the dilator 32 to rely solely on tactile sensations for guiding the dilatation shaft 42 within the body (see, e.g., FIGS. 20-21). By insufflating, distending, or irrigating with a fluid, e.g., a gas or a liquid, in applications such as laproscopy, e.g., in and around the abdomen, or arthroscopy, e.g., in or around the knee, the dilator 32 and system 30 enhance viewing and use of tools or instruments within the cavity or space for various medical procedures. For example, the dilator 32 and system 30 advantageously allow the taking of preliminary views in a very small hole to make sure no obstructions or problem areas are on the other side of a region such as tissue prior to insertion of surgical or other medical related tools or instruments.

More preferably, a sectional boundary of the dilatation shaft lumen 44, again, formed by taking a cross-section substantially perpendicular to a longitudinal axis extending through the center of the lumen 44, is formed by an intersection of five substantially cylindrical-shaped openings as illustrated in FIG. 7. The openings, specifically, can include first 100, second 102, third 104, fourth 106 and fifth 108 openings. Each opening, as illustrated, has a sectional diameter and a center point. Each of the first 100, second 102, and third 104 openings is positioned such that the cross-sectional diameter of each, $D_1$, $D_2$, and $D_3$, respectively, is substantially coincident, and the center point of each, $Cp_1$, $CP_2$, $CP_3$, respectively, is spaced-apart along an imaginary straight line L. The line L advantageously is coextensive with the sectional diameters of each of the first 100, second 102, and third 104 openings. Moreover, as also illustrated, the fourth 106 and fifth 108 openings each intersect with the second opening 102 at opposing boundaries of the second opening 102 such that each of the fourth 106 and fifth 108 openings have sectional diameters, D4 and D5, respectively, that are each coincident with an imaginary line P extending through the center point of the second opening $CP_2$ and substantially perpendicular to the imaginary line P coextensive with the cross-sectional diameters of the first, second, and third openings, D1, D2, and D3, respectively, such that the perimeter of the cross-section of the lumen 44 thereby defines a cavity having a central portion 102 around which are positioned four spaced-apart lobes 100, 104, 106, 108.

As perhaps best illustrated in FIGS. 10 and 12, the distal tip 40 of the dilatation shaft 42 is preferably tapered. The tapered tip 40 not only provides smoother entry of the dilatation shaft 42 into an opening in the body; it also means that the exposed perimeter of each lobe of the lumen 44 can have a substantially elliptical shape to thereby facilitate delivery of fluid via the lumen 44. Thus, while the shape of the lumen as described above will ensure that the outer perimeter of each lobe is at least substantially circular, tapering the tip further ensures that the lobes are elliptically shaped so as to further enhance the fluid delivery capability of the lumen 44.

By providing the lumen 44 with the particular structure described, fluid is delivered into a bodily opening, passageway, or cavity so as to more rapidly and more evenly fill the surrounding regions of the opening, passageway, or cavity. Accordingly, the fluid more readily provides a lubricity that facilitates the advance of the dilatation shaft 42. Likewise, the fluid is distributed so as to more uniformly create fluid pressure against the walls and tissue of the opening, passageway, or cavity. This fluid pressure adds to the forces of the dilatation shaft 42, spacer, 66, or cannula 68 so as to more readily and more evenly achieve dilatation of the opening, passageway, or cavity (see FIGS. 1-2 and 14-15).

According to the present invention, as perhaps best shown in FIGS. 1, 14-18, and 25-26, the dilator 32 further includes a substantially elongate cannula 68 adapted to be slidably positioned over at least a portion of the dilatation shaft. The dilator 32 also includes at least one spacer 66 adapted to be slidably positioned over at least a portion of the dilatation shaft 42 and slidably positioned within the cannula 68. Using the combination of the cannula 66 and at least one spacer 68 with the dilatation shaft 42, a bodily opening and/or cavity is dilated using the dilator 32 by a dilatation procedure referred to herein as stepped dilatation.

Various stepped dilatation procedures can be enabled by the combination of the present invention. For example, according to a first technique illustrated in FIGS. 16-18 and 22-24, the at least one spacer 66 and cannula 68 are positioned on the dilatation shaft 42 such that, initially, the at least one spacer 66 is within the cannula 68 and both are positioned on a proximal region of the distal portion 46 of the dilatation shaft 42. Thus, the arrangement of the cannula 68 and at least one spacer 66 creates a telescoped formation of overlapping sections. The first stepped dilatation is effected with the insertion of the exposed distal region of the dilatation shaft 42 of the dilator 32. After the smaller diameter shaft 42 is inserted into a bodily opening, the slightly larger diameter spacer is slid distally over the shaft 42 to effect another step increase in the dilatation of the opening. If a plurality of spacers is used, additional step increases in dilatation result as each spacer is slidably moved into place. Finally, in a last step increase in dilating the opening, the cannula 68 is slid distally over the last spacer. Once the desired degree of dilatation is achieved, the dilatation shaft 42 and each at least one spacer 68 can be withdrawn from within the cannula 68. The cannula 68 can be left in place to maintain the desired degree of dilatation. The cannula further provides an interface with conventional equipment (e.g., catheter, endoscope, or hysteroscope) for diagnosis or therapeutic treatment of the cavity, canal, actual or potential space or other opening of the body.

Figure 19:
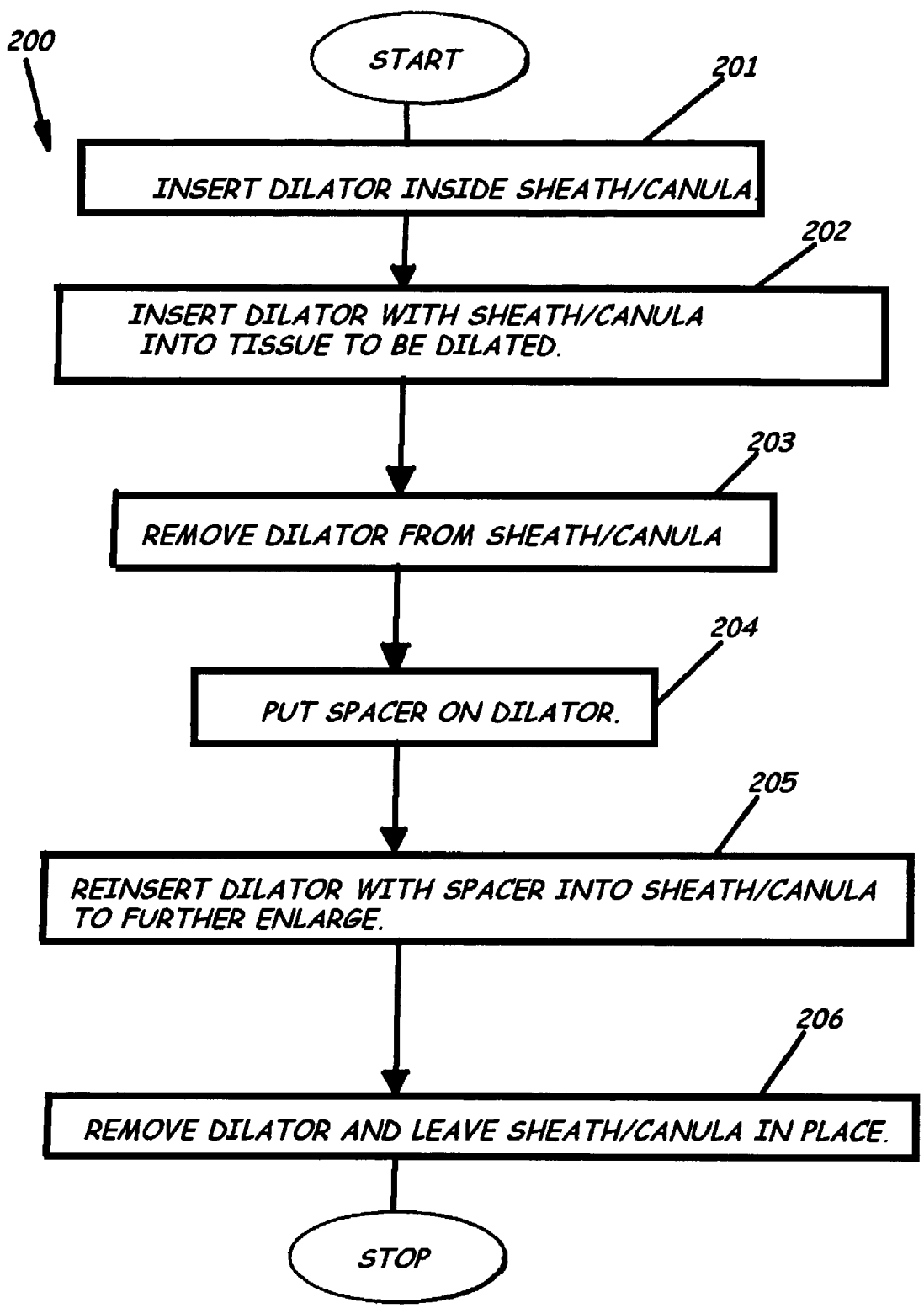
FIG. 19 is a flow diagram of a method of accomplishing stepped dilatation according to the present invention.

In yet a second technique or embodiment, at least the cannula 68' is made to radially expand when at least one spacer 66 is inserted therein (see FIGS. 19 and 25-26). According to this technique 200 (FIG. 19), the cannula 68' is positioned over the distal portion 46 of the dilatation shaft 42 (block 201) before the dilatation shaft is inserted into a bodily opening (block 203). After insertion, the dilatation shaft 42 is removed while the cannula 68' remains positioned within the bodily opening. A spacer 66, having a slightly larger (i.e., stepped) diameter than the cannula 68', is then positioned on the dilatation shaft 42 (block 204), and the dilatation shaft 42 with the spacer positioned thereon is reinserted into the cannula 68' so that the spacer 66 is slidably inserted into the cannula 68' (block 205). The slightly larger or stepped diameter of the spacer 66 increases the diameter of the cannula 68'. The dilatation shaft 42 and spacer 66 are then removed from within the cannula 68', which is left in place (block 206). If greater dilatation is required, the steps are repeated as necessary with successive spacers 66 of increased diameters.

In addition to the dilator 32, the dilatation system 30 as noted above further includes a handle 34. The handle 34 preferably is adapted to detachably connect to the dilator 32. The handle 34, moreover, can include a top surface 70 and a bottom surface 72. Formed in the bottom surface 72 of the handle 34, is a dilatation shaft channel 74 (see FIG. 2) positioned to detachably receive and retain therein the dilatation shaft 42. Preferably, a manifold channel 76 is also formed in the bottom surface 72 of the handle 34 to receive and retain the manifold 60, 60' therein. Preferably, at least one supply tube channel (78, 80) is also formed in the bottom surface 72 of the handle 34. More preferably, the at least one supply tube channel includes a first tube channel 78 and a second tube channel 80 each formed in the bottom surface 72 of the handle 34 to receive and retain therein at least first and second supply tubes 86, 88 respectively, which either alone or in combination can define the proximal end of the dilatation shaft 42.

According to the present invention, the handle 34 further includes a control actuator 84. Preferably the actuator 84 is positioned on a side portion or, more preferably, the top surface 70 of the handle 34. The control actuator 84 is adapted to engage the controller 56 of the dilatation shaft 42. To accommodate the engagement, a control opening 82 is formed in the handle 34 to receive therein the controller 49 including or connected to the at least one wire 50. Preferably, the opening 82 is formed in the bottom surface 72 of the handle 34 and extends therefrom through the top surface 70 of the handle 34 so as to permit at least a portion of the controller to extend through the control opening 82. More preferably, the control opening 82 is a control sleeve opening to accommodate a control sleeve 56 positioned on a medial portion 48 of the dilatation shaft 42. The control sleeve opening 82 thus allows at least a portion of the control sleeve 56 to extend through the opening 82 and engage the control actuator 84 positioned on the handle 34.

In a preferred embodiment of the handle 34, the handle 34 also preferably has a side portion 90 that is connected to the top 70 and bottom 72 surfaces of the handle 34 such that the handle 34 has substantially rounded or arcuate-shaped contours to facilitate the ready handling of the handle by a user. (See FIGS. 1-5, 8-13.) Also, the handle preferably has proximal, medial, and distal portions formed so that the lateral extent of the medial portion is greater than the lateral extent of the distal portion, and the lateral extent of the proximal portion is greater than the lateral extent of the medial portion to thereby form a substantially teardrop shape to also facilitate the ready handling of the handle 34 by a user. (See FIGS. 1-5, 8-13.) More specifically, the rounded contours and teardrop shape permit the handle 34 to fit easily in the hand of a user and allow the user to firmly and comfortably grip the handle 34 as the handle 34 is used to maneuver the dilator 32 attached thereto. The shape and contours, moreover, provide the user ready access to the control actuator 84 so that the control actuator 84 can be operated by the user using a thumb or finger of the hand holding the handle 34.

The handle 34 not only serves to maneuver the dilator 32 but also acts as a distal tip attitude indicator (see FIGS. 1, 8-9, and 11). Specifically, the handle 34 can be aligned so that the control actuator 84 or a surface portion of the handle 34 lie a plane parallel with the plane through which the distal tip 40 of the dilatation shaft 42 flexes. For example, the handle 34 can be formed such that a portion of the top 70 surface of the handle 34 is parallel with the plane in which the distal tip 40 moves in response to the user's moving, preferably and advantageously by sliding, the control actuator 84. Thus, the orientation of the handle 34 and the forwardly or rearwardly position of the control actuator 84 responsively indicate to a user the direction in which the distal tip 40 is pointing.

In addition to the dilator 32 and handle 34, the dilatation system 30 of the present invention preferably also includes at least one supply tube 86, 88 and 86', 88' capable of attaching to the at least one access port 62, 64 of the manifold 60, 60' and being positioned in fluid communication with the lumen 44 of the dilatation shaft 42. More preferably, the at least one supply tube includes at least a first supply tube 86, 86' and a second supply tube 88, 88'. Each preferably is connected to the first and second access ports 62, 64 respectively and positioned in fluid communication with the lumen 44, 44' within the proximal region 54, 54' of the medial portion of the dilatation shaft 42 (see FIGS. 28-29).

The dilatation system 30 preferably further includes a fiber optic scope 36 positioned to extend through the first supply tube 86, through the manifold 60, 60' or hub member, and through the dilatation shaft lumen 44. As discussed above, the positioning of a fiber optic scope 36 (or, alternatively, a camera-tipped scope or other imaging device) provides a visualization capability that enhances the steerability of dilatation shaft 42 of the dilator 32 as it is maneuvered through the contours and actual or potential spaces in a human or animal body (see FIGS. 20-21). In addition, the dilatation system 30 preferably also includes a fluid supply 38 in communication with the second supply tube 88 to deliver fluid into the human or animal body via the second supply tube 88 and the dilatation shaft lumen 44.

The multi-channeled structure of the handle 34 described above is such that it can readily be attached to the dilator 32. Specifically, the dilatation shaft channel 74, the manifold channel 76, and supply tube channels 78, 80, coupled with the control opening 82, allow the dilator 32 and handle 34, for example, to be simply "snapped" together. Thus, the dilator 32 can be readily attached to the handle 34 and, then, after use of the handle-connected dilator 32, be detached. The absence of intricate components or internal cavities within the handle 34 along with the lack of sharply angled contours makes sterilization of the handle by conventional means extremely easy.

Thus, the handle 34 can be repeatedly used if desired, while allowing each separate, single-use detachable dilator 32 to used once and thrown away. The combination of a disposable dilator 32 and a re-usable handle 34 offers major advantages over existing dilatation devices in at least the following respect. Because the dilator 32 has an internal cavity (i.e., the dilatation shaft lumen 44), it can be visually guided with a fiber optic scope 36, 36', as explained more fully below. This allows for visual guidance of the dilator 32 rather than forcing the user to rely simply on tactile sensation. The lumen 44 also permits delivery of a fluid into the body to thereby irrigate and/or distend and/or insufflate tissue, a particular advantage if as will frequently be the case the dilator 32 is within a collapsed potential space and to assist to allow stepped insertion of additional larger dilatation components such as spacers, cannulas, or other devices.

Thus, the lumen 44 provides visualization, irrigation, distension, and insufflation capabilities. Nevertheless, the lumen 44 is a cavity and like all cavities is difficult to sterilize. Various viruses, bacteria, and harmful disease carrying media can become lodged internally on the inner surface of the cavity or be trapped in the residual of lubricants or other organic materials used to coat the dilator when it is used with a patient. It is easier and less time consuming to simply dispose of the dilator 32 after each use. By making the dilator 32 controllable without relying on intricate internal mechanisms, it can be manufactured economically. Thus, it will be efficient if the dilator 32 is used only once and disposed of rather than sterilized. The handle 34, however, is easily sterilized and, hence, it can be economical to sterilize and re-use the handle if desired or otherwise can be made as understood by those skilled in the art to be disposable. Therefore, the combination provides significant advantage over conventional devices in that the dilator 32 provides visualization, irrigation, distension, and insufflation capabilities and yet is economically made. The handle 34 can be efficiently sterilized and reused. The present invention detachably connects or combines the two together to so as to economically achieve the benefits of both.

Figure 20:
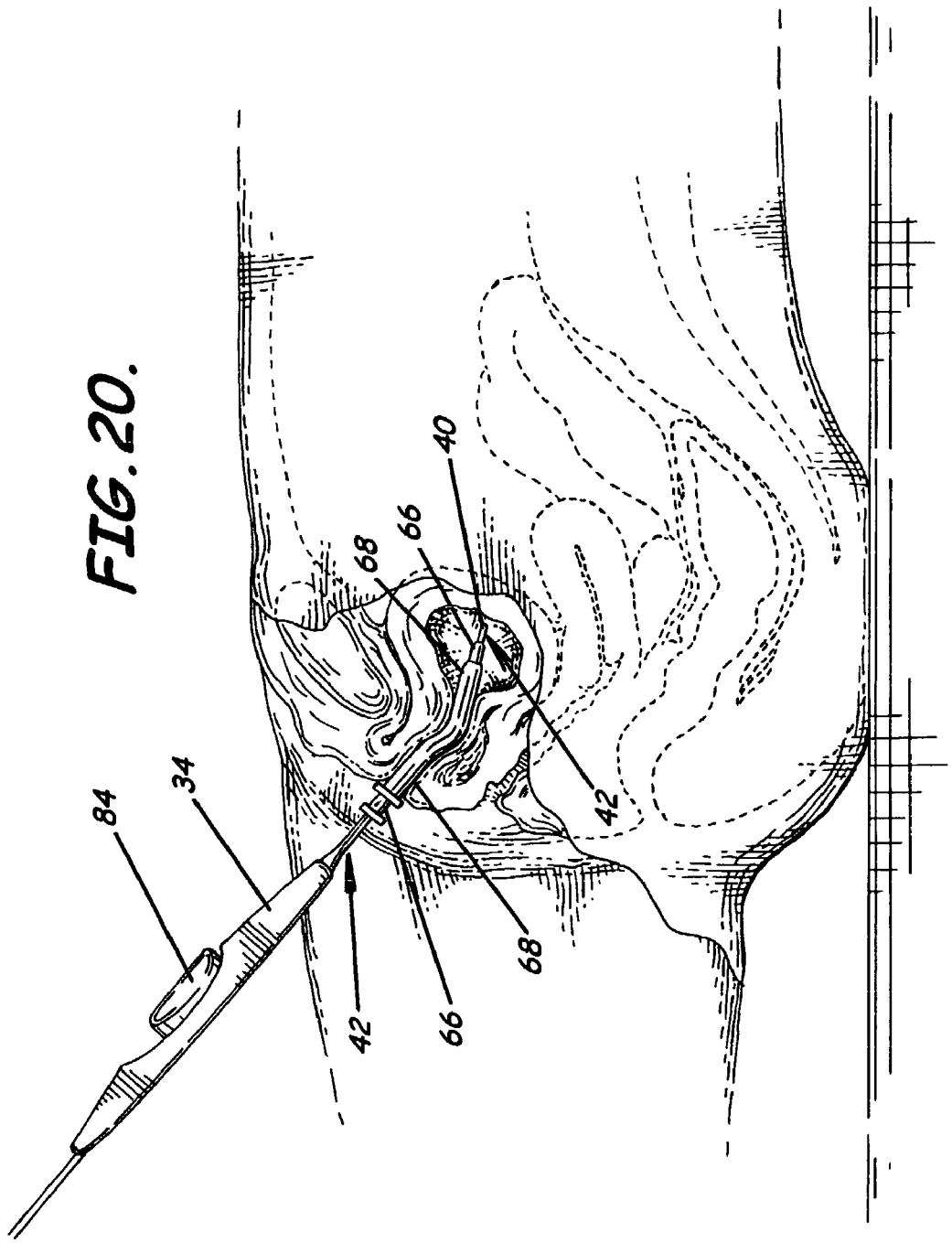
FIG. 20 is an environmental side elevation view of a dilator and detachable handle according to the present invention.
Figure 21:
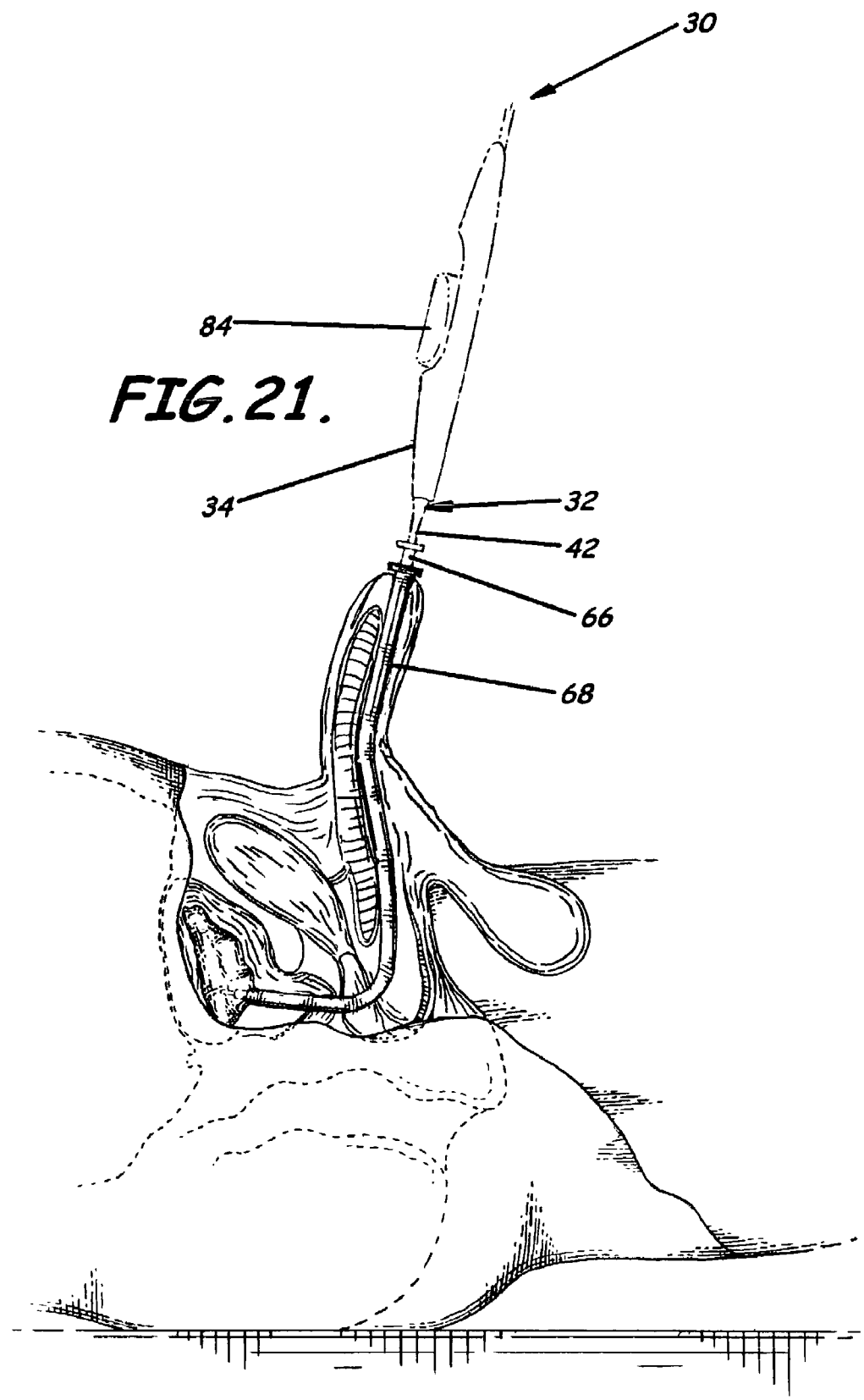
FIG. 21 is an environmental side elevation view of a dilator and detachable handle according to the present invention.

The structure of the control mechanism of the present invention is easily manufactured and yet it is more than adequate to enhance the controllability of the dilator 32 so that the dilatation shaft 42 can be better maneuvered through highly contoured regions and within collapsed potential spaces of a human or animal body such as shown in FIGS. 1 and 20-21. The control mechanism so described provides the further advantage of being easily engaged by the controller 49 of the handle 34 so that, again, the dilatation system 30 combines an economically produced dilator that has unique capabilities and can be coupled with the a detachable, easily sterilized, re-usable handle 34.

As perhaps best illustrated in FIG. 27, the present invention also provides a disposable dilator kit 116 that can be used by a physician or veterinarian for dilatation of a portion of a human or animal body using a visually guided steerable dilator. The kit 116 preferably includes a disposable container 118. Within the kit container 118 is contained a sanitized disposable steerable dilator 32 having a dilatation shaft and contained in a sanitary dilator package 120. The kit container 118 preferably also includes a sanitized disposable handle 34 adapted to detachably connect to the dilator 32 and which can also be contained in a sanitary handle package (not shown). Moreover, the kit container 118 preferably also includes a sanitized cannula 68 adapted to be slidably positioned substantially surround at least a portion of outer surfaces of the dilatation shaft of the dilator 32 and contained within a sanitary cannula package 120 in combination with the dilator 32 or alone in a separate package (not shown). The kit container 118 preferably also includes at least one spacer 66 adapted to be slidably positioned to substantially surround at least a portion of outer surfaces of the dilator 32 and to be positioned within the cannula 68.

The at least one spacer 66, or plurality of spacers if desired, is also preferably maintained in a sanitary spacer package 120, and the spacer and spacer package can be contained within the container 118.

The kit preferably includes a dilator 32 having a lumen 44 formed in the dilatation shaft 42 of the dilator 32. The dilator 32 further preferably has manifold 60, 60' or hub member connected to the dilatation shaft 42 and having at least one access port 62, 64 and 62', 64' (FIGS. 28-29) in fluid communication with the dilatation shaft lumen 44. The at least one access port is preferably adapted to connect to at least one supply tube. The kit container 118 can also further includes a fluid supply and one or more supply tubes if desired. The supply tube preferably is adapted to connect to the access port 64 to deliver fluid through the supply tube into the lumen 44 and through the lumen 44 into the body. The kit 116 can also include a sanitizable fiber optic scope and a supply tube adapted to accept therein the fiber optic scope.

As already described above, the present invention enables a number of distinct techniques for achieving dilatation of a bodily opening in a stepwise manner. Accordingly, the present invention includes distinct method aspects of step dilatation as shown in FIGS. 1-29 and as described herein. One such includes inserting a distal region 110 of the distal portion of a dilatation shaft 42 into an opening in the body. A proximal region 112 of the distal portion of the dilatation shaft preferably has at least one spacer 66 slidably positioned over at least a portion of the proximal region 112 of the distal portion of the dilatation shaft 42 with the cannula 68 slidably positioned over at least a portion of the at least one spacer 66. (See FIGS. 16-18 and 25-26.) From this position, the spacer 66 is slidably moved over at least a portion of the distal region 110 of the distal portion of the dilatation shaft 42, such as when a space is distended or being irrigated while the cannula 68 is substantially maintained in position over the proximal region 112 of the distal portion of the dilatation shaft 42 (see FIG. 17). Because the radial diameter of the spacer 66 is greater than that of dilatation shaft 42, advancing the spacer into the opening over the distal region 110 of the distal portion of the dilatation shaft 42 dilates the opening (see FIG. 18). Then, the cannula 68 is slidably moved over at least a portion of the spacer 66 while substantially maintaining the spacer 66 slidably positioned over at least a portion of the distal region 110 of the distal portion of the dilatation shaft 42 (see FIG. 26).

These steps preferably are repeated in stepwise fashion. The distal region of the distal portion of the dilatation shaft 42 is slidably advanced further within the opening in the body, beginning the advance from a position in which the at least one spacer 66 is positioned over the distal region 110 of the distal portion of the dilatation shaft 42 and in which the cannula 68 is positioned over at least a portion of the spacer 66. Because the cannula 68 and at least one spacer 66 remain substantially in place as the dilatation shaft 42 is slidably advanced through the cannula 68 and the at least one spacer 66 further into the opening, the advance then terminates at position in which the at least one spacer 66 is positioned over the proximal region 112 of the distal portion of the dilatation shaft 42 and in which the cannula 68 is substantially positioned over at least a portion of the at least one spacer 66.

The method preferably includes visualizing a potential space within the body using a fiber optic scope 36 (or camera-tipped scope 36' or other imaging device as understood by those skilled in the art) positioned within a lumen 44 formed in the dilatation shaft 42. The method preferably further includes distending potential space and tissue within the body, the distension being accomplished using a fluid delivered via the lumen 44 of the dilatation shaft 42.

An alternative method according to the present invention relies on using a cannula 68' having at least a medial portion adapted to radially expand in response to a spacer 66'. The method is perhaps best illustrated by FIGS. 19, 28 and 29. The spacer 66' preferably is selected to have a larger radial diameter than that of the cannula 68' being positioned therein. (See FIGS. 28 and 29.) Specifically, as illustrated in FIG. 19, the method includes inserting the distal portion of the dilatation shaft 42, over which the cannula 68' is slidably positioned, into an opening in the body. The dilatation shaft 42 is then slidably withdrawn and separated from the body and the cannula 68', leaving the cannula 68' inserted in the opening in the body. At least one spacer 66' is then slidably positioned over the dilatation shaft 42, after which both the at least one spacer 66' and dilatation shaft 42 are slidably reinserted into the cannula 68' to thereby radially expand at least the medial portion of the cannula 68' and the opening in which the cannula is positioned.

The at least one spacer 66' of the method preferably is a first spacer and the method further can include slidably positioning a second spacer over the dilatation shaft 42 and slidably inserting the dilatation shaft 42 and second spacer into the cannula 68' to thereby further radially expand, in stepwise or gradual fashion, at least the medial portion of the cannula 68' and the opening in which the cannula is positioned.

The method preferably further includes visualizing a potential space within the body using a fiber optic scope 36 (or camera-tipped scope 36') positioned within a lumen 44 formed in the dilatation shaft 42. The fiber optic scope 36 allows a physician to view the opening, passageway, or cavity into which the dilatation shaft 42 is extended so that the physician is not limited to relying solely on tactile sensation in steering the dilator 42.

The method also preferably includes distending tissue within the body with a fluid delivered via the lumen 44 of the dilatation shaft 42. The fluid delivered into the body aids step dilatation by, for example, increasing lubricity in and around the dilator 32 thereby reducing frictional resistance to the advancement of the dilatation shaft 42 within an opening, passageway, or cavity within the body. The fluid also creates fluid pressure against the tissue making up the walls of the opening, passageway, or cavity. Thus, as the dilatation shaft 42 is advanced into the body and as step dilatation proceeds within a bodily opening the fluid pressure adds to the forces provided by contact of the dilatation shaft 42, spacer 66, and cannula 68 causing further distension of tissue and further dilating the bodily opening. The fluid delivery, therefore, both irrigates and provides fluid pressure to enhance the process of step dilatation.

In the drawings and specification, there have been disclosed typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

That claimed is:

1. A dilatation system comprising:
   a dilator having a dilatation shaft, the dilatation shaft having a medial portion and a malleable distal portion including a flexible distal tip, the medial portion including a distal region having a distal region diameter and a proximal region having a proximal region diameter, the distal region diameter being greater than the proximal region diameter;
   a detachable handle detachably connected to the dilator;
   a fiber optic scope adapted to be positioned within the dilatation shaft;
   a fluid delivery supply in fluid communication with the dilatation shaft; and
   a controller associated with the dilator to control the attitude of the flexible distal tip of the malleable distal portion of the dilatation shaft, the controller comprising a control sleeve associated with the medial portion of the dilatation shaft and connected to at least one control wire extending axially from the distal tip to the proximal portion of the dilatation shaft on which the control sleeve is slidably positioned, the control sleeve substantially surrounding the proximal region of the medial portion of the dilatation shaft so as to slidably move over the proximal region to thereby increase tension in the at least one control wire and cause the distal tip of the dilatation shaft to flex in response thereto.

2. A system as defined in claim 1, wherein the dilatation shaft includes a lumen extending axially therethrough.

3. A system as defined in claim 2, wherein the dilatation shaft has a perimeter of a sectional boundary of the dilatation shaft which defines a cavity having a central portion around which are positioned a plurality of spaced-apart lobes substantially contiguous with the central portion, a section of the sectional boundary being taken substantially perpendicular to a longitudinal axis extending through the center of the lumen.

4. A system as defined in claim 3, wherein the tip of the dilatation shaft is substantially tapered to reduce resistance to the advancement of the dilator within a body opening and also further facilitate the delivery of fluid through the lumen with the fiber optic scope positioned therein, and wherein the tapered tip of the dilatation shaft exposes the perimeter of each lobe of the lumen so that the opening has a substantially elliptical shape thereby facilitating delivery of fluid through the lumen.

5. A system as defined in claim 2, wherein the lumen is formed by an intersection of five substantially cylindrical-shaped openings so that the perimeter of the lumen defines a cavity having a central portion around which are positioned four spaced-apart lobes substantially contiguous with the central portion, and wherein a perimeter of the lumen permits the fiber optic scope to be positioned in the dilatation shaft so that it extends axially substantially through the central portion of the lumen while also permitting fluid to be delivered through the lumen to thereby allow visually guiding of the fiber optic scope as it is advanced within a bodily opening when the fiber optic scope is positioned in the lumen of the dilatation shaft.

6. A system as defined in claim 2, wherein the dilator further includes a manifold attached to a proximal end of the dilatation shaft, the manifold including at least one access port in fluid communication with the lumen of the dilatation shaft.

7. A system as defined in claim 6, wherein the at least one access port includes at least a first and a second access port attached to which, respectively, is a first supply tube and a second supply tube, wherein the fiber optic scope is adapted to be extended through the first supply tube into the lumen and extended through the lumen to the distal tip of the dilatation shaft, and wherein the fluid delivery supply is adapted to deliver fluid to the lumen through the second supply tube.

8. A system as defined in claim 1, wherein the handle is detachably connected to the dilator and engages the controller associated with the dilatation shaft and the distal tip, the handle including a dilatation channel formed therein so that the dilatation shaft can be readily received and retained therein and a manifold channel formed in the handle to receive and retain therein a manifold of the dilator.

9. A system as defined in claim 8, wherein the handle further includes at least one supply tube channel also formed in the handle to receive and retain therein at least one supply tube connected to the manifold of the dilator and a control actuator positioned thereon and adapted to readily engage the controller associated with the dilator when the dilator is detachably connected with the handle, the control actuator being positioned to be responsive to finger or thumb deflection supplied by a user holding the handle and controllably steering the dilator using a single hand.

10. A dilatation system comprising:
    a dilator having a dilatation shaft, the dilatation shaft having a medial portion and a malleable distal portion, the medial portion including a distal region having a distal region diameter and a proximal region having a proximal region diameter, the distal region diameter being greater than the proximal region diameter, the malleable distal portion including a flexible distal tip;
    a handle connected to the dilator; and
    a controller associated with the dilator to control the attitude of the flexible distal tip of the malleable distal portion of the dilatation shaft, the controller including a control sleeve connected to at least one control wire extending axially from the distal tip to a proximal portion of the dilatation shaft on which the control sleeve is slidably positioned, the control sleeve substantially surrounding the proximal region of the medial portion of the dilatation shaft so as to slidably move over the proximal region of the medial portion to thereby increase tension in the at least one control wire and cause the distal tip of the dilatation shaft to flex in response thereto.

11. A system as defined in claim 10, wherein the dilatation shaft includes a lumen extending axially therethrough.

12. A system as defined in claim 11, wherein the dilator further includes a manifold attached to a proximal end of the dilatation shaft, the manifold including at least one access port in fluid communication with the lumen of the dilatation shaft.

13. A system as defined in claim 12, wherein the at least one access port includes at least a first and a second access port attached to which, respectively, is a first supply tube and a second supply tube, wherein a fiber optic scope is adapted to be extended through the first supply tube into the lumen and extended through the lumen to the distal tip of the dilatation shaft, and wherein a fluid delivery supply is adapted to deliver fluid to the lumen through the second supply tube.

* * * * *